United States Patent [19]

Techer et al.

[11] 4,337,263
[45] Jun. 29, 1982

[54] 1-ARYL-4-γ-ARYLSULPHONYL-3-AMINO-PROPOXY-1H-PYRAZOLES AND THEIR USE AS HYPOLIPEMIANT AND HYPOCHOLESTEROLEMIANT AGENTS

[75] Inventors: Henri Techer, Avon; Gilles Monnier, Creteil; Marcel Pesson, Paris, all of France

[73] Assignee: Laboratoire Roger Bellon, Neuilly sur Seine, France

[21] Appl. No.: 164,566

[22] Filed: Jun. 30, 1980

[30] Foreign Application Priority Data

Jul. 5, 1979 [FR] France .................. 79 17507

[51] Int. Cl.³ ............... A61K 31/415; A61K 31/505; A61K 31/535; C07D 231/28
[52] U.S. Cl. .................. 424/273 P; 424/248.5; 424/263; 548/374; 548/376; 544/140; 546/211
[58] Field of Search .............. 548/374, 376; 544/140; 546/211; 424/273 P, 248.5, 263

[56] References Cited

U.S. PATENT DOCUMENTS

3,700,688 10/1972 Iwai et al. ............... 548/375
4,008,249 2/1977 Fischer et al. ............ 548/374

FOREIGN PATENT DOCUMENTS

34517 10/1965 Finland .
2301250 9/1976 France .

OTHER PUBLICATIONS

Alberty et al., Chem. Abst. 1967, vol. 67, No. 43, 734t.

Primary Examiner—Henry R. Jiles
Assistant Examiner—N. Harkaway
Attorney, Agent, or Firm—Eyre, Mann, Lucas & Just

[57] ABSTRACT

1-Aryl-4-γ-arylsulphonyl-3-aminopropoxy-1H-pyrazoles of the formula:

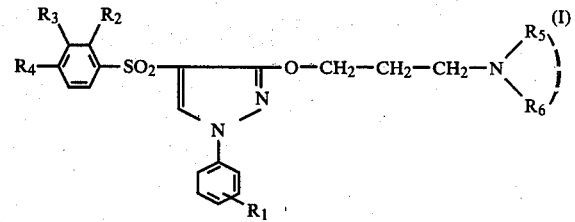

and their acid addition salts.

Application of these compounds as medicaments useful in particular as hypolipemiant or hypocholesterolemiant agents.

9 Claims, No Drawings

1-ARYL-4-γ-ARYLSULPHONYL-3-AMINO-PROPOXY-1H-PYRAZOLES AND THEIR USE AS HYPOLIPEMIANT AND HYPOCHOLESTEROLEMIANT AGENTS

DESCRIPTION

The present invention relates to derivatives of 1H-pyrazole characterised by the presence on the heterocyclic ring of an aryl group (which may itself be substituted) at the 1-position, a γ-aminopropoxy group (N-mono- or di-substituted) at the 3-position and an arylsulphonyl group (which may be substituted) at the 4-position, as well as their non-toxic pharmaceutically-acceptable acid addition salts.

The compounds according to the invention correspond to the general formula:

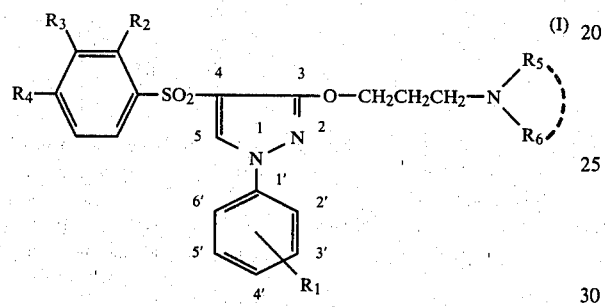

wherein:
$R_1$ represents a hydrogen or halogen atom or a $C_{1-3}$ alkyl, $C_{1-3}$ alkoxy or trifluoromethyl radical in the meta or para position on the phenyl group,
$R_2$, $R_3$ and $R_4$ are the same or different and each represents a hydrogen or halogen atom or a $C_{1-3}$ alkyl, $C_{1-3}$ alkoxy or trifluoromethyl group, and
$R_5$ and $R_6$ are the same or different and each represents a hydrogen atom or a $C_{1-3}$ alkyl radical or $R_5$ and $R_6$ together represent, with the nitrogen atom to which they are attached, a 5- or 6-membered heterocyclic group optionally containing another hetero-atom, and the non-toxic pharmaceutically-acceptable acid addition salts thereof.

In the definitions of the groups $R_1$ to $R_4$, the alkyl or alkoxy groups have from 1 to 3 carbon atoms and this is also intended when reference is made herein to "lower alkyl" and "lower alkoxy" groups.

More particularly, in the preferred compounds of formula I, $R_1$, $R_2$, $R_3$ and $R_4$ are the same or different and each represents a hydrogen, fluorine, chlorine or bromine atom or a methyl, methoxy or trifluoromethyl group, $R_5$ and $R_6$ are the same or different and each represents a hydrogen atom or a methyl or ethyl group or $R_5$ and $R_6$ together represent, with the nitrogen atom to which they are attached, a morpholino, piperidino or pyrrolidino group.

It is known that 1,4-diaryl-ω,N-monoalkyl and N-dialkyl-3-aminoalkoxy-pyrazoles have analgesic and antiinflammatory properties (French Patent application No 2,301,250). It has been found, in a suprising and unexpected manner, that the compounds according to the invention, mainly characterised by the presence of a 4-arylsulphonyl group on the pyrazole ring, as well as their salts with non-toxic acids, have hypocholesterolemiant and hypolipemiant properties which are susceptible of therapeutic use.

When $R_5$ and $R_6$ each represent a lower alkyl group or are included in a heterocyclic group as defined above, the compounds of the invention can be obtained by condensing a 1-halogeno-3-dialkylaminopropane (III), preferably a 1-chloro-3-dialkylaminopropane, with the salt of a 1-aryl-4-arylsulphonyl-1H-pyrazolol-3 and an alkali metal M (II):

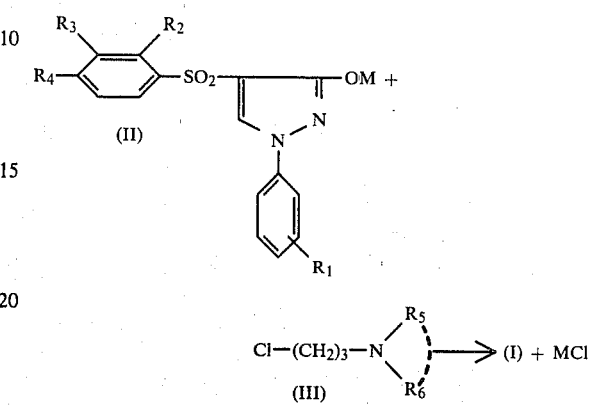

As the alkali metal, sodium or potassium is preferably used.

The reaction is carried out at a temperature in the range from 60° to 120° C., in a solvent or a suitable mixture of solvents. The use of a lower tertiary aliphatic alcohol, such as tert.-butyl alcohol, is particularly desirable. In order to facilitate dissasociation of the salt (II), it is also desirable to add to the medium a dipolar aprotic solvent, such as DMF or DMSO. Preferably, DMF is used in an amount of ½ to 1 volume per volume of alcohol employed.

In principle, the reaction requires the use of equimolar proportions of the metal derivative (II) and the halogeno derivative (II). However, it is preferable to utilise a slight excess of the latter.

The metal derivative (II) is advantageously prepared in situ by the addition of one molecule of a 1-aryl-4-arylsulphonyl-pyrazolol-3 to a solution of an alcoholate of an alkyli metal (for example, potassium), obtained by dissolving a gram-atom of the metal in an excess of the tertiary alcohol.

If required, a suitable volume of DMF is added to the solution (or suspension) of the metal derivative (II) and then a slight excess (1.1 to 1.2 mole) of a 1-chloro-3-dialkylaminopropane is added and the mixture is agitated and heated, in the absence of moisture, at a temperature in the range from 60° to 100° C. until the end of the reaction, which requires 5 to 8 hours.

The solvent(s) is/are eliminated by distillation under vacuum and the residue is taken up in water. The reaction product is extracted with a suitable solvent. The organic solution is washed with a dilute solution of alkali metal hydroxide (to eliminate unreacted pyrazolol) and then with water. It is dried ($K_2CO_3$) and filtered. The solvent is eliminated by distillation under vacuum. The crystalline residue is purified by recrystallisation from a suitable solvent.

The bases (I) are converted into non-toxic mineral or organic acid salts by known procedures.

According to a modification, the products of the invention can be obtained by the reaction of primary or secondary amines with 1-aryl-4-arylsulphonyl-pyrazoles, substituted at the 3-position by a propoxy chain, itself carrying at the γ-position a substituent X' allowing a displacement reaction with the basic reactant (V):

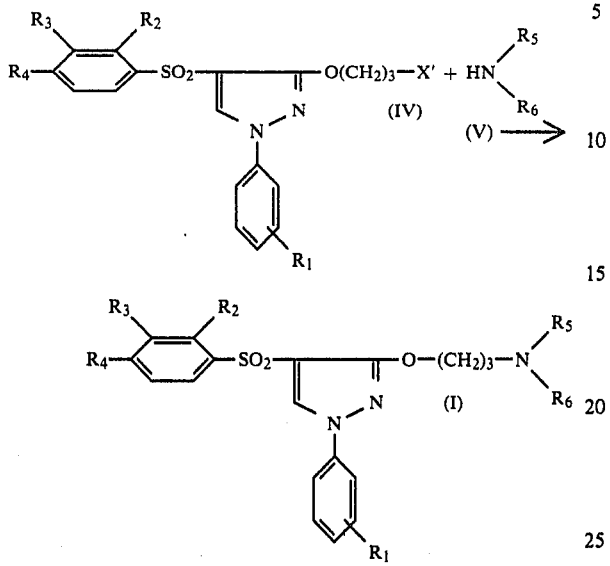

For this purpose, use can be made of compounds (IV) where X' represents a halogen atom, such as chlorine, bromine or iodine, an arylsulphonyloxy radical or, preferably, an alkylsulphonyloxy radical, particularly a methylsulphonyloxy (mesyloxy) radical.

The reaction of the compounds (IV) and the amines (V) is conducted at temperatues in the range from 50° to 150° C.

It is recommended to utilise an excess of amine, in the ratio of at least 2.5 moles of the latter per mole of the compound (IV) employed, the excess serving as an acceptor for the acid molecules formed in the reaction. It is also possible to utilize the amine (V) only in a slight excess, provided an acid acceptor is added to the medium, which can be a tertiary aliphatic amine, such as triethylamine, a basic heterocyclic substance such as pyridine or one of its higher methylated homologues, or a basic mineral agent, such as alkali metal carbonate.

With amines having a boiling point of at least 80° C. operation can proceed in the presence of an excess of amine acting as the solvent or by heating the reactants under reflux, in a solvent having a suitable boiling point, preferably selected from lower alcohols and aromatic hydrocarbons.

With amines having boiling points lower than 80° C., operation can occur in an autoclave in one of the solvents mentioned above.

Within the limits of the temperatures and concentrations defined above, the reaction is generally terminated after 2 to 6 hours of heating. The solvent and the excess of amine are eliminated by distillation under vacuum. The residue is taken up in a dilute solution of a strong mineral acid or preferably methane-sulphonic acid. The solution is filtered and then rendered alkaline by the addition of a concentrated solution of alkali metal hydroxide. The product of the reaction is extracted with a suitable solvent. It is isolated and purified, as indicated above.

The intermediate compounds (IV) are obtained by known procedures starting from the corresponding alcohol (VI):

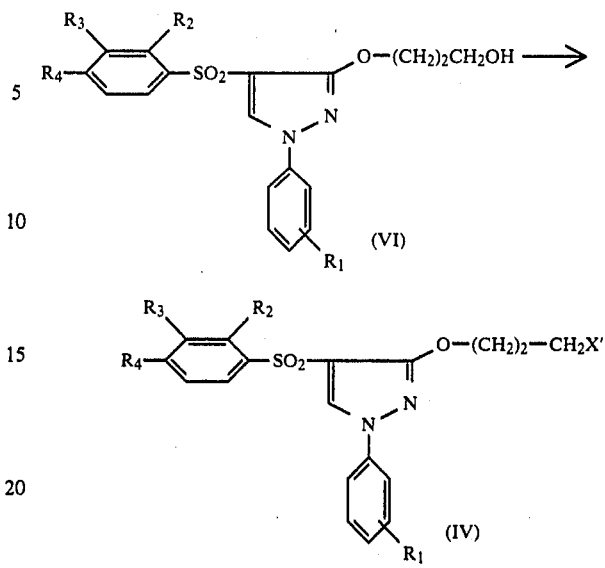

In particular, the methanesulphonyloxy compounds (X'=—OSO$_2$CH$_3$) are obtained by the action of methane-sulphochloride on alcohols (VI) in aprotic solvents, such as chloroform, dichloromethane or aromatic hydrocarbons, such as benzene. Operation takes place in the presence of hydracid acceptors such as tertiary aliphatic amines or pyridic bases.

The alcohols (VI) are obtained by the reaction of 3-chloropropanol with a salt of a 1-aryl-4-arylsulphonyl-1H-pyrazolol (II):

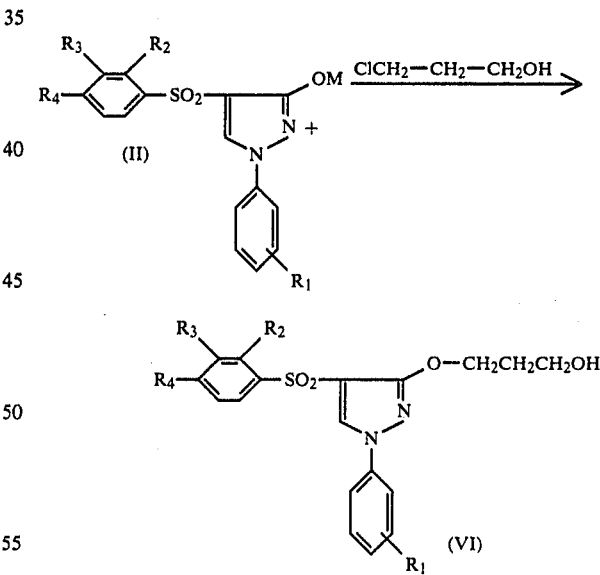

The reaction is preferably conducted in a non-polar aprotic solvent such as toluene, possibly including 20% to 50% of a polar aprotic solvent such as DMF, which allows the best solubilisation of the metal derivative (II).

The latter is obtained by the action of an anhydrous alcoholate (1 mole) on the 1-aryl-4-arylsulphonyl-1H-pyrazolol-3, in a solvent or a mixture of solvents as defined above.

The reaction between the metal derivative (II) (1 mole) and the 3-chloropropanol is preferably conducted in the presence of a slight excess of the latter (1.1 to 1.2 mole) at a temperature in the range from 80° to 120° C. Under these conditions, the reaction is terminated after 15 to 20 hours of heating. The reaction product is isolated, as indicated in French Patent Application No 2301250 for the analogous compounds derived from the 1,4-diaryl-1H-pyrazoles.

The 1-aryl-4-arylsulphonyl-1H-pyrazolol-3 compounds (XII), the metal salts (II) of which are utilised for the preparation of the compounds according to the invention, are substances which have not previously been described.

The compounds (XII) can be obtained by two methods.

(1) According to a first method (procedure A), the 1-aryl-4-arylsulphonyl-1H-pyrazolol-3 compounds are obtained according to known procedures, by the oxidation of 1-aryl-4-arylmercapto-pyrazolol-3 compounds (XI). The latter are themselves unknown; their preparation can be effected by a procedure similar to that described by the applicants in French Patent Application No 2301250 for obtaining the 1,4-diaryl-1H-pyrazolol-3 compounds:

12 to 18 hours at ordinary temperature. The sodium derivative of the malonaldehydate (VIII) is so obtained, which is extracted from the mixture with water. The aqueous solution is acidified with a strong mineral acid. The ethyl-arylmercaptomalonaldehydate thus liberated is extracted with a suitable solvent. The combined extracts are washed with water and dried ($Na_2SO_4$). Evaporation of the solvent leaves the crude malonaldehydate, which is sufficiently pure for the following operation. The yields are in the range from 80% to 100%.

(b) According to the procedures described in the aforementioned French patent application, an ethyl arylthiomalonaldehydate (VIII) is first condensed with an ethyl arylcarbazate (IX) to give a β-(2-ethoxycarbonyl-2-arylmercapto)-vinylcarbazate (X) which without being isolated is directly cyclised into a 1-aryl-4-arylmercaptopyrazolol-3.

The condensation of the malonaldehydate (VIII) and the arylcarbazate (IX) is conducted, as is known, by heating the two compounds in equimolar proportions under reflux in a solvent having a boiling point in the range from 80° to 150° C. and giving an azeotrope with

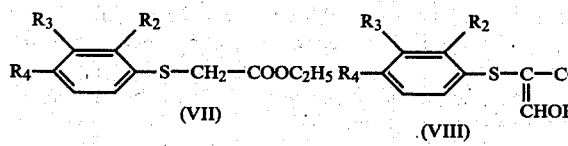
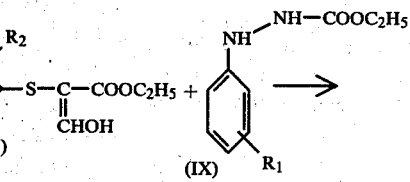
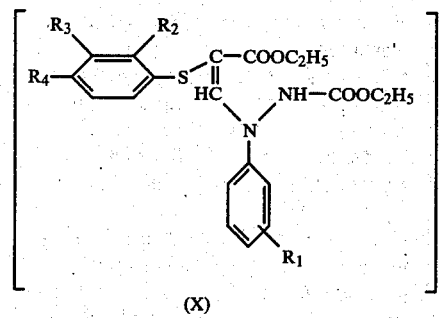
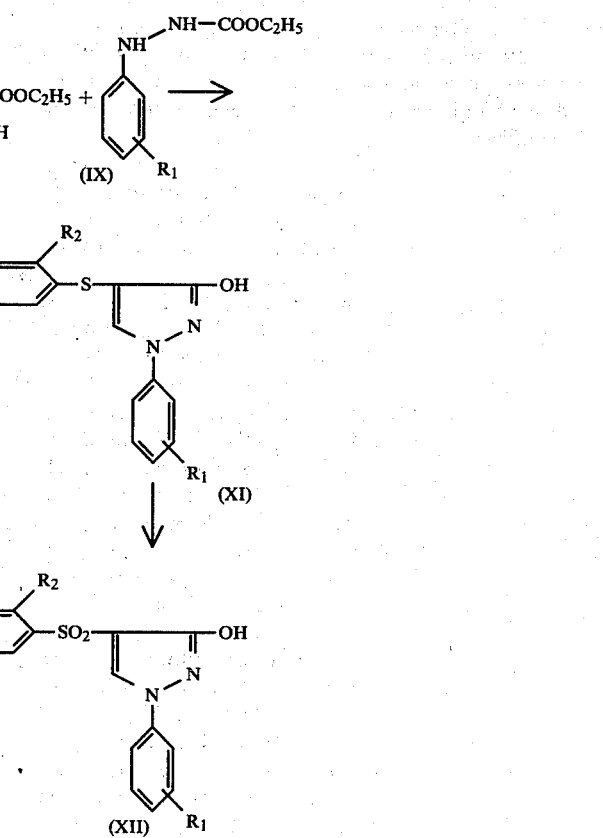

(a) Starting with a lower alkyl arylthioacetate, preferably the ethyl compounds, an ethyl arylthiomalonaldehydate (VIII) is prepared in a manner known per se. For this purpose, the arylthioacetate (1 mole) and an excess of ethyl formate (2 to 3 moles) are condensed, in the presence of a slight excess (1.1 to 1.3 mole) of a lower alcoholate of an alkali metal, in a non-polar neutral solvent, preferably an aromatic hydrocarbon, such as benzene or toluene.

The reaction is preferably conducted first at low temperature (0° to 5° C.) and then the mixture is left for water evolved in the reaction. Preferably, benzene or toluene is used. The water is recovered in a suitable separator which allows the course of the reaction to be followed and for it to be arrested when the quantity of water formed no longer increases.

Cyclisation of the intermediate (X) so obtained can be effected directly in the reaction mixture, by the addition of 1 mole (or a slight excess: 1.1 to 1.2 mole) of an alcoholate of an alkali metal in solution in the corresponding alcohol.

The reaction is conducted under reflux. The pyrazolol salt (XI) precipitates in the medium. After cooling, the salt is dried and then dissolved or suspended in water. Acidification of the medium to pH 5 with a mineral or organic acid liberates the pyrazolol (XI) which is then dried, washed with water and recrystallised from a suitable solvent.

Industrially, it can be more advantageous to effect the cyclisation of the intermediate (X) with an alkali metal hydroxide, preferably potassium hydroxide. In this case, when the reaction between the malonaldehyde (VIII) and the arylcarbazate (IX) is terminated, the solvent is eliminated by distillation under vacuum. The residue is dissolved in a lower alcohol, preferably ethanol or methanol, and potassium hydroxide is added to the solution as a concentrated aqueous solution. A quantity of the reactant is utilised which is sufficient to neutralise the carbon dioxide formed in the reaction. By operating at 50° to 60° C., the reaction is terminated in 30 minutes. The pyrazolol is isolated and purified as before.

(c) Oxidation of the 1-aryl-4-arylmercapto-1H-pyrazolols (XI) to the 1-aryl-4-arylsulphonyl-1H-pyrazolols (XII) can be effected by any of the methods generally utilised for this kind of reaction. The use of hydrogen peroxide as the oxidising agent in an acetic acid medium is particularly advantageous and preferably is utilised.

In this case, the arylmercapto derivative (XI) (1 mole) is dissolved or suspended in 10 to 20 volumes of acetic acid. The mixture is agitated and an excess of perhydrol (3 to 5 moles) is added and then the mixture is taken to 80° C.

The reaction is generally terminated in 3 to 5 hours. During this time, the starting material which is initially insoluble passes into solution and then the reaction product precipitates.

After cooling, the mixture is diluted with an equal volume of water, the sulphone (XII) which is insoluble is dried, washed with water, dried and then recrystallised from a suitable solvent. Frequently, the crude product is sufficiently pure to be utilised directly for preparation of the compound according to the invention.

(2) The second method (procedure B) comprises 2 stages.

In a first stage, a lower alkyl arylsulphonylacetate (XIII) is condensed with an arylhydrazine (XIV) and gives a β-arylsulphonylacetylhydrazine (XV).

In a second stage, this arylsulphonylhydrazine is cyclised into the corresponding pyrazolol-3, by the action of a derivative of formic acid corresponding to the general formula $HC-X_1X_2X_3$:

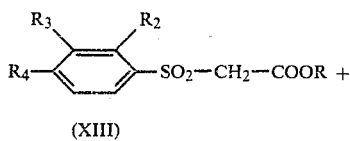

(XIII)

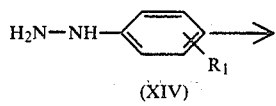

(XIV)

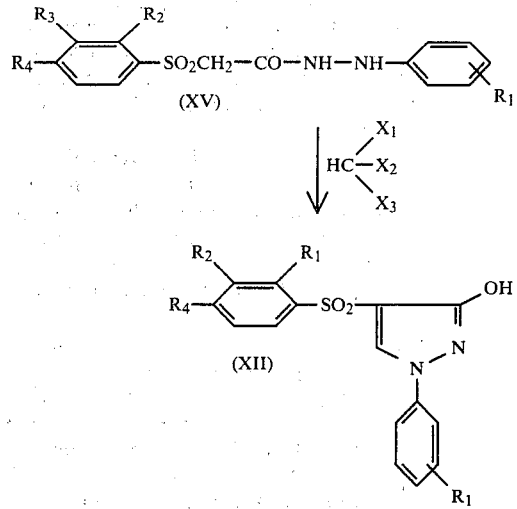

The reaction of a lower alkyl arylsulphonylacetate (XIII) with an arylhydrazine (XIV) cannot be obtained directly by simple heating of the two reactants.

According to a modification of the invention, it is possible to effect this condensation by operating in the presence of a strong organic base, particularly a tertiary aliphatic amine, such as triethylamine, tributylamine or triethanolamine which favours the reaction.

The mixture of the alkyl arylsulphonylacetate (1 mole), the arylhydrazine (1 mole) and the tertiary base (1 mole) is heated to a temperature in the range from 40° to 100° C. To ensure complete reaction of the ester (XIII), it may be necessary to utilise an excess of the hydrazine (XIV) (1.1 to 1.5 mole). Then, use is made of the corresponding excess of the tertiary amine.

In order to avoid oxidation of the hydrazine during the reaction, it is preferable to operate under a nitrogen atmosphere.

The reaction can also be conducted in a solvent having a boiling point at least equal to the temperature of the reaction. Use is thus made of a quantity of the solvent such that the combined reactants in it have a concentration of 10% to 50%.

The solvents utilisable are preferably selected from those known to favour the aminolysis of esters, such as butanol, glycol, 2-methoxy-ethanol and 2-ethoxy-ethanol. Of these, use is most advantageously made of those which are entirely miscible with water, which facilitates isolation of the reaction product.

As lower alkyl arylsulphonylacetates, use can be made of non-branched $C_1$ to $C_5$ alkyl esters, but it is recommended to employ preferably the methyl esters, which are the most reactive. When using the latter either in a dry manner or in the presence of a solvent (for example, glycol) and operating under the conditions defined above at 50° C., the reaction is generally terminated after 12 hours of heating. When the mixture is cooled, it is diluted with water, which causes precipitation of the hydrazide (XV) which is dried, washed with water and recrystallised from a suitable solvent.

As well as has already been mentioned, heterocyclisation of the arylhydrazide (XV) can be effected by treatment of the latter by means of a reactive derivative of formic acid which corresponds to the general formula $HC-X_1X_2X_3$. Among the compounds of this type which are most frequently used in similar reactions, there can be mentioned:

(a) lower alkyl orthoformates ($X_1=X_2=X_3=OR$), more particularly methyl or ethyl orthoformate, (b) the diacetals of dimethylformamide, ($X_1=X_2=OR, X_3= -N(CH_3)_2$), particularly dimethylaminoacetal, ($-OR= -O-CH_3$), (c) bisdimethylaminoalkoxymethanes, ($X_1=X_3= -N(CH_3)_2$, $X_2= OR$), particularly bisdimethylaminomethoxymethane and bisdimethylamino-tertiary-butoxymethane.

Study of the use of the various reactants in the reaction of cyclisation of the compounds (XV) has shown that use of the orthoformates is not appropriate in this case. Under the conditions usually utilised for reactions of this type (heating of a compound XV) (1 mole) with an excess of ethyl or methyl orthoformate (3 to 4 moles) in the presence of acetic acid), the pyrazolol-3 compounds (XII) are obtained only in poor yields.

Heating at 90°-100° C. for 5 to 12 hours of a hydrazide (XV) (1 mole) in solution in DMF, with a dialkylketal of dimethylformamide, (for example dimethylketal) or a bisdimethylaminoalkoxymethane (for example, bisdimethylamino-tertiary-butyloxymethane) in excess (1.1 to 1.5 mole), provides a compound of the enamine type (XV):

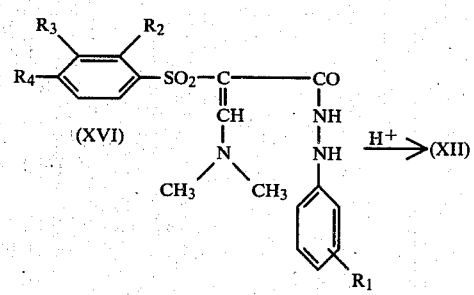

The latter, which is not isolated, is treated in aqueous solution with a strong mineral acid which leads to the cyclised product (XII) in good yields (80–90%).

However, the dialkylketals of dimethylformamide and the bisdimethylaminoalkoxymethanes are expensive reactants and their preparation is delicate and relatively long. Their use such as described above is a difficult application on an industrial scale.

According to a method according to the invention, these disadvantages can be remedied by preparing a solution in dimethylformamide of a bisdimethylaminoalkoxymethane which has not been isolated. This solution is utilised directly for the reaction with the hydrazide.

The principle of preparation of bisdimethylaminoalkoxymethanes has been described by H. Bredereck et col. (Chem Ber, 1968, 101, pages 41–50). The method (equation A) consists in reacting in a non-polar anhydrous medium an alkali metal alkoxide with a dimethyl formamidinium salt:

Equation A

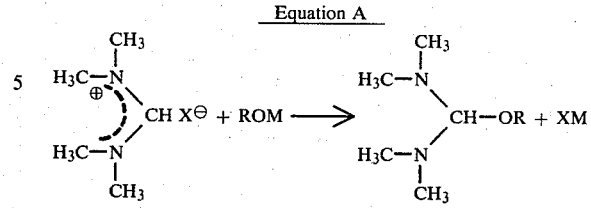

The formamidinium salts are obtained by a delicate preparation. However, arylsulphonates, notably benzene sulphonate (XVII), are easily obtained according to H. Ulery (J Org Chem, 1965, 30, 2464–2465 (equation B):

Equation B

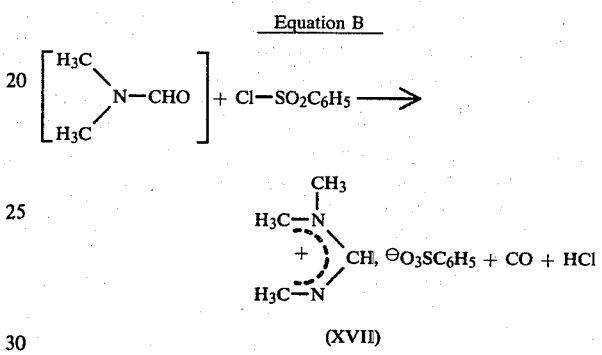

(XVII)

Operation proceeds for instance by heating, under gentle reflux for 4 hours, 1 mole of benzene sulphochloride in 2.5 to 3 times its own volume of DMF. Under these conditions, the benzenesulphonate (XVII) forms quantitatively and crystallises on cooling to a temperature below 30° C. Isolation of this salt is rendered difficult by reason of its hygroscopicity.

The applicants have established that:

(a) under the conditions of reaction B, the hydrochloric acid formed remains quantitatively in solution in the DMF;

(b) if this solution is treated with a sufficient quantity of an anhydrous alkali metal alcoholate, to neutralise this acid and ensure reaction of the formamidinium salt according to equation A (namely, 2 moles of alcoholate for 1 mole of benzene sulphochloride), a solution of bisdimethylaminoalkoxymethane is obtained, which can be employed directly for heterocyclisation of the hydrazides (XV).

To carry out this reaction, heating of a hydrazide (XV) (1 mole) is effected under a stream of nitrogen, at a temperature in the range from 80° to 100° C., in the presence of an excess of the reactant prepared as indicated above, for 5 to 6 hours. After cooling, the solution is diluted with 2 to 4 times its volume of water. It is adjusted to pH 3 to 4 by the addition of a strong mineral acid. The pyrazolol (II) which precipitates is dried and recrystallised from a suitable solvent.

In this operation to ensure complete reaction of the hydrazide, an excess of the reactant is preferably used, obtained by treating 1.1 to 1.5 mole of benzenesulphochloride per 1 mole of hydrazide.

The novel 1-aryl-4-arylsulphonyl-γ-mono and dialkyl-3-aminopropoxy-pyrazoles (I) according to the invention, are hypocholesterolemiant and hypolipemiant agents of a new type.

For therapeutic utilisation of these substances, preferably their acid addition salts with pharmaceutically-acceptable acids are used, such as for example, hydrochloric, hydrobromic, nitric, sulphuric, phosphoric, acetic, lactic, citric, tartaric, oxalic, benzoic, succinic, maleic, methanesulphonic, ethanesulphonic, camphosulphonic, benzenesulphonic and paratoluenesulphonic acids etc.

The products are administered orally in one of the forms generally utilised for this purpose, namely tablets, capsules, pills, powders, aqueous suspensions and syrups. In these forms, the active agents can be alone or associated with various carriers or inert pharmaceutically-acceptable vehicles. Also, various sweetening or perfumed substances generally utilised for this purpose can be added.

In particular, use can be made of tablets containing 0.010 to 0.050 g of the active compounds and comprising various excipients, such as sodium citrate, calcium carbonate and dicalcium phosphate, as well as various disintegrating ingredients such as starch (particularly tapicoa or potato starch), alginic acid and various complex silicates, as well as bonding agents such as saccharose, gum arabic or polyvinylpyrrolidone. The tablets can also comprise lubricating agents generally utilised for facilitating tableting, such as talc, magnesium stearate or sodium laurysulphate.

By way of illustrative example, tablets have been prepared having the following composition:

|  | For 1 Tablet |
|---|---|
| Active compound (Example 1) | 10 mg |
| Lactose | 102 mg |
| Wheat starch | 70 mg |
| Saccharose | 25 mg |
| Carboxymethylcellulose | 9 mg |
| Magnesium stearate | 4 mg |
|  | 220 mg |

The 220 mg tablets so obtained are coated with a solution of saccharose to obtain pills each weighing 415 mg.

Similar solid compositions can be utilised to fill hard or soft gelatin capsules.

To obtain aqueous solutions or elixirs, for administration orally, the active compound can be associated with various sweetening, aromatic or colouring agents and if required emulsifying agents or can be put into suspension, accompanied by diluents such as water, ethanol, propyleneglycol, glycerol or various associated substances.

The total daily dosage should preferably be from 0.030 to 0.150 g divided into 2 or 3 administrations per 24 hours.

The following non-limitative examples are given by way of illustration of the preparation of compounds according to the invention.

EXAMPLE 1

4-para-chlorophenylsulphonyl-3-γ-dimethylaminopropoxy-1-phenyl-1H-pyrazole (I, $R_1=R_2=R_3=H$, $R_4=Cl$, $R_5=R_6=-CH_3$)

In a 3 liter 3-necked flask provided with an agitator, a bromine ampoule, a thermometer and an upright condenser, a solution of potassium tert-butoxide was prepared by the dissolution of 21.5 g (0.55 gram-atom) of potassium in 440 cm$^3$ of tertiary butanol. 180 g (0.595 mole) of 4-parachlorophenylsulphonyl-1-phenyl-1H-pyrazolol-3 and 450 cm$^3$ of dimethylformamide were then added.

The mixture was heated for 30 minutes under reflux. After cooling to 30° C., 78.5 g (0.646 mole) of N-(3-chloropropyl)-dimethylamine was added. The reaction was conducted by heating under reflux, without agitation, for 5 hours.

The major part of the solvents was eliminated by distillation over a water-bath under vacuum produced by a water-pump (12 mm Hg). The residue was taken up in 400 cm$^3$ of water. The aqueous suspension was extracted with methylenechloride (400 cm$^3$, then 2×200 cm$^3$). The combined extracts were washed with 2 N caustic soda (3×75 cm$^3$) and then with a saturated solution of sodium chloride (200 cm$^3$). The organic solution was dried over $K_2CO_3$ and decolourised by agitation with animal charcoal. It was filtered and concentrated to dryness under vacuum produced with a water-pump. The residue was recrystallised from ethanol (440 cm$^3$). 183 g (yield=81%) of 4-parachlorophenyl-sulphonyl-3-γ-dimethylaminopropoxy-1-phenyl-1H-pyrazole was obtained, MP=109° C.

Analysis for $C_{20}H_{22}ClN_3O_3S$ (MW: 419.92): Calculated % C 57.20, H 5.28, N 10.01, Cl 8.44: Found % C 57.49, H 5.48, N 9.81, Cl 8.51.

Methanesulphonate 41.9 g of methanesulphonic acid was added to 183 g of the preceding base, in solution in 900 cm$^3$ of ethyl acetate. The precipitate was dried and recrystallised from an acetone-isopropyl oxide mixture. 196 g (yield=87%) of 4-parachlorophenylsulphonyl-3-dimethylaminopropoxy-1-phenyl-1H-pyrazole methanesulphonate was obtained, melting point=151° C.

Analysis for $C_{20}H_{22}ClN_3O_3S,HO_3SCH_3$ (MW: 516.03): Calculated % C 48.88, H 5.08, N 8.14: Found % C 48.82, H 5.13, N 8.37.

The process described in Example 1 was repeated to prepare the compounds of Examples 2 to 17, starting with suitably substituted 1-aryl-4-arylsulphonyl-1H-pyrazolol-3 compounds. The base constants obtained as well as those of their methanesulphonates are given in Table I below.

EXAMPLE 18

(a) A solution of potassium tertiary butoxide was prepared by dissolving 4.8 g of the metal (0.123 gram-atom) in 100 cm$^3$ of tert-butanol. The solvent in excess was eliminated by evaporation under vacuum, in the absence of moisture, under a nitrogen atmosphere. To the dry alcoholate so obtained, a solution of 40 g of 4-parachlorophenylsulphonyl-1-phenyl-1H-pyrazolol-3 in a mixture of 90 cm$^3$ of DMF and 360 cm$^3$ of toluene was added. The mixture was agitated and heated for 30 minutes under reflux. 12.4 g (0.13 mole) of 3-chloropropanol was then added. The reaction was terminated by heating under reflux and agitating for 20 hours.

The solvents were eliminated by concentration under vacuum (12 mm Hg) at 100° C. The residue was taken up in 90 cm$^3$ of 2 N KOH, to dissolve the unreacted pyrazolol. The aqueous suspension was extracted with 200 cm$^3$ and then 2×100 cm$^3$ of ethyl acetate. The combined organic solutions were washed with water, dried over $K_2CO_3$ and decolourised by agitation with animal charcoal. After filtration, they were evaporated to dryness at 100° C. under vacuum.

The solid residue was recrystallised from ethanol (100 cm³). 16.5 g of 4-parachlorophenylsulphonyl-3-γ-hydroxypropoxy-1-phenyl-1H-pyrazole was obtained, MP=109° C.

Analysis for $C_{18}H_{17}ClN_2O_4S$ (MW: 392.86): Calculated % C 55.03, H 4.36, N 7.13, Cl 9.03, S 8.16: Found % C 54.81, H 4.43, N 7.28, Cl 9.22, S 8.10.

(b) 5.4 g (0.053 mole) of triethylamine was added to a solution of 13 g of the foregoing alcohol (0.035 mole) in 70 cm³ of methylene chloride. The mixture was agitated and cooled to −10° C. 4.5 g (0.039 mole) of methanesulphochloride was then added dropwise. After agitating for 30 minutes at 0° to 5° C., the solution was poured into 25 cm³ of iced water. The organic phase was separated by decantation. It was washed successively with water, sodium bicarbonate solution and then again with water. It was dried (Na₂SO₄) and then filtered to dryness under vacuum. The solid residue was recrystallised from 250 cm³ of ethanol. 15.1 g of 4-parachlorophenyl-sulphonyl-3-γ-methanesulphoxypropoxy-1-phenyl-1H-pyrazole was obtained, MP=114° C.

Analysis for $C_{19}H_{19}ClN_2O_6S_2$ (MW: 470.95): Calculated % C 48.45, H 4.07, N 5.95, Cl 7.53, S 13.62: Found % C 48.88, H 4.16, N 6.16, Cl 7.75, S 13.22.

(c) 4.3 g of the foregoing ester (0.009 mole) and 4.1 g of dimethylamine (0.09 mole) in 40 cm³ of ethanol were heated for 7 hours at 90° C. in a 100 cm³ steel autoclave.

After cooling, the solvent and the excess amine were eliminated by concentration under vacuum.

The residue was dissolved in 40 cm³ of an N solution of methanesulphonic acid. The solution was filtered to separate a small amount of insoluble material, extracted with ether (3×20 cm³) and then rendered alkaline by the addition of caustic soda. The precipitate was extracted with methylene chloride (3×50 cm³). The combined organic solutions were washed with water and then dried (K₂CO₃). After filtration, they were concentrated to dryness under vacuum. 3.1 g (yield=81%) of 4-parachlorophenylsulphonyl-3-γ-dimethylamino-propoxy-1-phenyl-1H-pyrazole was obtained, MP=109° C., identical to the product described in Example 1.

EXAMPLE 19

4-p-chlorophenylsulphonyl-3-γ-morpholinopropoxy-1-phenyl-1H-pyrazole 7 g (0.015 mole) of the ester prepared according to Example 18(b) and 7.8 g (0.09 mole) of morpholine were heated for 8 hours at 95° C. The excess amine was eliminated by distillation under vacuum (12 mm Hg) at 100° C. The residue was dissolved in 100 cm³ of 0.5 N methanesulphonic acid. After filtration, the solution was rendered alkaline by the addition of caustic soda. The reaction product was isolated as described in Example 18(c). The crude base was recrystallised from 80 cm³ of ethanol. 6.3 g (yield=92%) of 4-parachlorophenylsulphonyl-3-γ-morpholinopropoxy-1-phenyl-1H-pyrazole was obtained, MP=144° C.

Analysis for $C_{22}H_{24}ClN_3O_4S$ (MW: 461.96): Calculated % C 57.20, H 5.24, N 9.10, Cl 7.68, S 6.94: Found % C 57.23, H 5.28, N 9.24, Cl 7.83, S 6.70.

Methanesulphonate 1.2 g of methanesulphonic acid was added to 5.8 g of the base in solution in 200 cm³ of acetone. The precipitate was dried and recrystallised from 120 cm³ of ethanol. 6.3 g (yield=89%) of the salt was obtained, MP=225° C.

Analysis for $C_{22}H_{24}ClN_3O_4S,HO_3SCH_3$ (MW: 558.87): Calculated % C 49.50, H 5.06, N 7.53, Cl 6.35, S 11.49: Found % C 49.88, H 5.18, N 7.50, Cl 6.34, S 11.25.

EXAMPLE 20

4-p-chlorophenylsulphonyl-3-γ-methylaminopropoxy-1-phenyl-1H-pyrazole 15 g (0.032 Mole) of the ester described in Example 18(b) and 32 g of 33% aqueous methylamine were dissolved in 150 cm³ of ethanol. The mixture was heated for 7 hours at 90° C. in an autoclave. After cooling, the product of the reaction was isolated as described in Example 18(c). It was purified by recrystallisation from hexane. 19 g (yield=83%) of 4-parachlorophenylsulphonyl-3-γ-methylaminopropoxy-1-phenyl-1H-pyrazole was obtained, MP=74° C.

Analysis for $C_{19}H_{20}ClN_3O_3S$ (MW: 405.90): Calculated % C 56.22, H 4.97, N 10.35, Cl 8.74, S 7.90: Found % C 56.00, H 5.03, N 10.37, Cl 8.68, S 8.10.

Methanesulphonate 1.9 g of methanesulphonic acid was added to 8 g of the base in solution in 160 cm³ of ethyl acetate. The precipitate was dried and recrystallized from acetone. 8.4 g of the salt was obtained, MP=148° C.

Analysis for $C_{14}H_{20}ClN_3O_3S,HO_3SCH_3$ (MW: 502.00): Calculated % C 47.85, H 4.82, N 8.37, Cl 7.06, S 12.77: Found % C 47.89, H 4.97, N 8.63, Cl 7.22, S 12.89.

EXAMPLE 21

4-p-chlorophenylsulphonyl-3-γ-ethylaminopropoxy--phenyl-1H-pyrazole 7.9 g (0.017 mole) of the ester described in Example 18(b) and 7.6 g (0.17 mole) of ethylamine in solution in 100 cm³ of ethanol were heated for 7 hours at 90° C. in an autoclave. The reaction product was isolated as indicated in Example 18(c). It was purified by recrystallisation from isopropyl oxide. 6 g (yield =85%) of 4-parachlorophenyl-sulphonyl-3-γ-ethylaminopropoxy-1-phenyl-1H-pyrazole was obtained, MP=97° C.

Analysis for $C_{20}H_{22}ClN_3O_3S$ (MW: 419.92): Calculated % C 57.20, H 5.28, N 10.00, Cl 8.44, S 7.64: Found % C 56.90, H 5.21, N 10.05, Cl 8.36, S 8.00,

Methanesulphonate 1.3 g of methanesulphonic acid was added to 5.8 g of the base in solution in 200 cm³ of ethyl acetate. The precipitate was recrystallised from acetone. 6.3 g (yield=88%) of the salt was obtained, MP=149° C.

Analysis for $C_{20}H_{22}ClN_3O_3S, HO_3SCH_3$ (MW: 516.03): Calculated % C 48.87, H 5.08, N 8.14, Cl 6.87, S 12.43: Found % C 48.65, H 5.08, N 8.20, Cl 7.15, S 12.44,

EXAMPLE 22

4-p-chlorophenylsulphonyl-3-γ-piperidinopropoxy-1-phenyl-1H-pyrazole 6.85 g of the mesylic ester described in Example 18(b) and 7 g of piperidine were heated for 4 hours at 100° C. on a water-bath. The excess piperidine was eliminated by distillation under vacuum. The reaction product was isolated as indicated in Example 18(c). It was purified by recrystallisation from isopropyl oxide (150 cm³). 3.7 g of the base, which melted twice, MP=115° C., solidification, then MP=160° C., was obtained.

Analysis for $C_{23}H_{26}ClN_3O_3S$ (MW: 459.98): Calculated % C 60.05, H 5.70, Cl 7.71, S 6.97: Found % C 60.40, H 5.81, Cl 7.79, S 6.95.

2 cm³ of a 4 N solution of HCl in ethanol was added to 3.3 g of the base in solution in 100 cm³ of ethyl acetate. The precipitate was dried and then dried over phosphoric acid under vacuum. 3.5 g of the hydrochloride was obtained, MP=206° C.

EXAMPLE 23

4-p-chlorophenylsulphonyl-1-phenyl-3-γ-pyrrolidinyl-propoxy-1H-pyrazole 4.07 g of the mesylic ester described in Example 18(b) and 1.36 g of pyrrolidine in solution in 20 cm³ of toluene were heated for 3 hours at 90° C. The solvent was evaporated under vacuum and the residue was taken up in 20 cm³ of a 2 N methanesulphonic acid solution. The reaction product was isolated as indicated in Example 18(c). After recrystallisation from isopropyloxide, 2.6 g of the base was obtained, MP=125° C.

Analysis for $C_{22}H_{24}ClN_3O_3S$ (MW: 445.96): Calculated % C 59.25, H 5.42, N 9.42: Found % C 59.40, H 5.53, N 9.63.

2 cm³ of 4 N HCl in ethanol was added to 2.45 g of this base in solution in 75 cm³ of ethyl acetate. The precipitate was dried and then dried under vacuum over phosphoric acid. 2.6 g of the hydrochloride was obtained, MP=210° C.

EXAMPLE 24

4-p-chlorophenylsulphonyl-1-phenyl-1H-pyrazolol-3

This example illustrates the preparation according to Procedure A of the pyrazolol-3 compounds utilised to obtain the compounds according to the invention.

(a) Ethyl p-chlorophenylthiomalonaldehydate 38 g of sodium (1.66 gram-atom) was dissolved in 450 cm³ of absolute ethanol. The excess alcohol was eliminated by distillation under vacuum (12 mm Hg) at 100° C. under a nitrogen atmosphere. The dry sodium ethoxide so obtained was recovered with 750 cm³ of toluene and the mixture was vigorously agitated in the absence of air and moisture. It was externally cooled. A mixture of ethyl parachlorophenyl-thioacetate (346 g, 1.5 mole) and ethyl formate (222 g, 3 moles) was added dropwise over 1 hour at a temperature in the range from 0° to 5° C. The mixture was agitated during a further 2 hours at 5° C. and then left overnight at ordinary temperature.

The suspension of the sodium enolate was taken up in 900 cm³ of ice water with agitation. The aqueous phase was separated and the organic phase was washed with 100 cm³ of N NaOH. The alkaline extracts were combined with the aqueous phase and then adjusted to pH 1 by the addition of concentrated HCl. The reaction product was extracted with ether (3×500 cm³). The organic solution was dried (Na₂SO₄) and then filtered. The solvent was evaporated under vacuum (12 mm Hg) at 40° C. 377 g (yield=97%) of ethyl parachlorophenyl-thiomalonaldehydate was obtained, sufficiently pure for the following operation.

(b) 4-p-chlorophenylthio-1-phenyl-1H-pyrazolol-3

In a 1 liter flask (provided with an agitator, a bromine ampoule and a Dean-Stark separation connected to an upright condenser), a mixture of toluene (320 cm³), ethyl 3-phenyl-carbazate (144 g, 0.8 mole) and ethyl parachlorophenyl-thiomalonaldehydate (207 g, 0.8 mole) was heated under reflux with agitation. The reflux was maintained until the quantity of water formed in the reaction no longer increased, which required approximately 3 hours.

The solvent was eliminated by distillation under vacuum (12 mm Hg) at 100° C. The oily residue was dissolved in 220 cm³ of methanol. The solution was taken to 50° C. and a solution of potassium hydroxide (158 g) in 100 cm³ of water was added to it. This addition was conducted at such a rate that heating caused by the reaction maintained a controllable reflux of the solvent, which required about 1 hour. The mixture was agitated for a further 30 minutes. After cooling, 1100 cm³ of water was added and in order to dissolve the salts which had precipitated. The solution was carefully acidified (massive evolution of carbon dioxide) by means of concentrated hydrochloric acid (220 cm³).

After agitation for 1 hour at ordinary temperature, the precipitate was dried, washed with water and dried under vacuum over phosphoric acid. 181 g (75%) of 4-parachlorophenylthio-1-phenyl-1H-pyrazolol-3 was obtained, MP=214° C. For analysis, a sample was recrystallised from 2-methoxy-ethanol.

Analysis for $C_{15}H_{11}ClN_2S_2$ (MW: 302.78): Calculated % C 59.50, H 3.66, N 9.25, Cl 11.71: Found % C 59.52, H 3.86, N 9.05, Cl 11.93.

(c) In a 3000 cm³ three-necked flask provided with an agitator, a bromine ampoule, a thermometer and an upright condenser, a suspension of 181 g (0.6 mole) of the pyrazolol described in (b) in 1800 cm³ of glacial acetic acid was agitated. 180 cm³ (1.8 mole) of 30% perhydrol was then added. The mixture was agitated and heated at 80° C. for 4 hours. During this time, the first material passed into solution and then the product of the reaction partially precipitated.

After returning to ordinary temperature, 1800 cm³ of water was added to the reaction mixture. The precipitate was dried, washed with water and dried at 80° C. 145 g (73%) of 4-paraclorophenylsulphonyl-1-phenyl-1H-pyrazolol-3 was obtained, MP=215° C.

Analysis for $C_{15}H_{11}ClN_2O_3S$ (MW: 334.78): Calculated % C 53.81, H 3.31, N 8.37, Cl 10.59: Found % C 53.71, H 3.49, N 8.30, Cl 10.75.

EXAMPLE 25

Operating as described in Example 24(b) and utilizing suitably-substituted ethyl arylthioacetates and ethyl 3-aryl-carbazates, the 1-aryl-4-arylmercaptopyrazolol-3 compounds having the constants indicated in Table II below have been prepared.

By oxidation by means of perhydrol, as indicated in Example 24 (c), the corresponding sulphones were obtained having the constants given in Table IV below.

EXAMPLE 26

4-p-chlorophenylsulphonyl-1-phenyl-1H-pyrazolol-3

This example illustrates the preparation according to Procedure B of pyrazolol-3 compounds utilised to obtain the compounds according to the invention.

(1)
β-(2-p-chlorophenylsulphonyl-acetyl)-phenylhydrazine

In a three-necked flask connected to a mechanical agitator, a gas inlet, a thermometer and an upright condenser provided with a CaCl$_2$ trap, a mixture of methyl 2-parachlorophenylsulphonyl acetate (224 g, 0.9 mole), ethyleneglycol (540 cm$^3$), phenylhydrazine (146 g, 1.35 mole) and triethylamine (180 cm$^3$, 1.3 mole) was heated to 50° C. for 12 hours under agitation and under an anhydrous nitrogen stream.

From the start of the heating, the starting materials passed into solution. The reaction product commenced to precipitate after 4 hours.

The mixture was cooled and diluted with 1100 cm$^3$ of water. The precipitate was dried, washed with water and dried at 50° C.

2.7 g (yield=74%) of $\beta$-(2-parachlorophenylsulphonyl-acetyl)-phenylhydrazine was obtained, MP=171° C.

For analysis, a sample was recrystallised from ethanol, MP=171° C.

Analysis for C$_{14}$H$_{13}$ClN$_2$O$_3$S (MW: 324.79): Calculated % C 51.77, H 4.03, N 8.63, Cl 10.92, S 9.87: Found % C 51.65, H 4.14, N 8.46, Cl 10.92, S 9.40.

(2) Heterocyclisation (a) A solution of N,N,N',N'-tetramethylformamidiniumbenzene-sulphonate was prepared by adding 74.2 g (0.42 mole) of benzene-sulphochloride to 210 cm$^3$ of anhydrous DMF. The mixture was agitated in the absence of moisture for 2 hours at ordinary temperature and then heated for 4 hours under reflux. The solution was cooled to 30° C. in order to avoid crystallisation of the reactant, which can occur at excessively low temperatures.

(b) In a four-neck 3 liter flask provided with a mechanical agitator, a thermometer, a bromine ampoule and an upright condenser (provided with a solid sodium carbonate trap) and a dry nitrogen inlet, 32.8 g (0.84 gram-atom) of potassium was dissolved with agitation in 670 cm$^3$ of tertiary butanol.

The condenser was then put into the downward position and connected to a receiver, itself connected to a vacuum water-pump through the intermediary of a drying tube (CaCl$_2$) in order to avoid the entry of moisture into the apparatus. The excess tertiary butanol was eliminated under vacuum (20 mm) at 100° C.

210 cm$^3$ of anhydrous DMF was added to the dry potassium tertiary butoxide so prepared. The suspension was agitated and maintained under a dry nitrogen stream. A solution of tetramethylformamidinium benzenesulphonate prepared according to (a) and maintained at 30° C. was then added. The mixture was agitated for 3 hours at ordinary temperature under a nitrogen atmosphere in the absence of moisture.

91 g (0.28 mole) of $\beta$-(2-parachlorophenylsulphonyl-acetyl)-phenylhydrazine was rapidly added. While maintaining the nitrogen stream and the agitation, the temperature was adjusted to and maintained at 90° C. for 5 hours, during which the dimethylamine formed in the reaction was evolved.

After cooling to ordinary temperature, the mixture was taken up in 800 cm$^3$ of water. The solution was agitated and adjusted to pH 3-4 through the addition of concentrated HCl (35 cm$^3$). The solid was dried, washed with water and dried at 80° C. 88 g (90%) of 4-parachlorophenylsulphonyl-1-phenyl-1H-pyrazolol-3 was obtained, MP=216° C., identical to the product described in Example 24(c).

By replacing the potassium tertiary butoxide in (b) with the equivalent quantity of sodium methoxide, the same product was obtained in an identical yield.

EXAMPLE 27

Operating as described in Example 26-(1) and starting from suitably substituted methyl $\beta$-arylsulphonylacetates and optionally substituted phenylhydrazines, the corresponding $\beta$-(2-arylsulphonylacetyl)-arylhydrazines, whose constants are described in Table III below, were obtained.

The constants of the I-aryl-4-arylsulphonylpyrazolol-3 compounds utilised for the preparation of the compounds of the invention of Examples 1 to 23 are described in Table IV below.

The products according to the invention have a marked hypolipemiant activity, both as to cholesterol and as to triglycerides. The intensity of these actions depends upon the nature of the substituents $R_1$, $R_2$, $R_3$ and $R_4$.

With a view to ascertaining the activity of the various products and selecting those susceptible of more detailed study, there has first been carried out for each of them an approximate determination of the DL$_{50}$ in mice, (with oral administration), as well as research into hypolipemiant activity with oral administration in rats subjected to a normal alimentary regime.

Acute Toxicity in Mice

Three groups of 10 male mice each weighing 20–22 g respectively received doses of 100, 300 and 1000 mg/kg of the product studied, in solution in distilled water. The different doses were administered in a volume of solvent such that 0.5 cm$^3$ of solution per 20 g of animal weight was used. The mortality was observed throughout seven days. For examples 1 and 9, the DL$_{50}$ was ascertained and determined graphically according to the logprobit method.

Hypolipemiant Action

Groups of 10 male Wistar rats weighing 225–250 g were subjected to a normal alimentary regime.

For 4 days, the product being studied was administered orally, in solution in distilled water, at the rate of 10 cm$^3$ of solution per kg of body weight. On the fifth day after a fast lasting 17 hours, the animals were lightly anaesthetised with ether and were subjected to venus puncture in the retro-orbital sinus. With the blood thus obtained, the cholesterol (by the Liebermann method) and the triglycerides (Kessler and Lederer methods) ere measured for each animal.

The animals wer killed and the livers were weighed.

In paralle, a control group of 10 rats was treated in he same fashion but only received water. The same eterminations as before (cholesterol, triglycerides, liver weight) were carried out on each animal in tis group.

The variations in the various parametrs of the animals treated were expressed as percentages with respect to the same parameters of the control animals.

The results are set out in Table V below. The doses administered were selected as a function of the product of Example 1 for which the minimum active dose is of the order of 5 mg/kg. The substances have been assayed at double this dose. In the case of the least active compounds, the activity of a dose of 50 mg/kg has been ascertained.

In Table V, only variations equal to or greater than 10% are considered as indicating an activity. Examination of Table V shows that most of the compounds in the invention are active for at least one of the two parameters: cholesterol and/or triglycerides.

By way of comparison, clofibrate (ethyl parachlorophenoxyisobutyrate) was subjected to the same test. This product has a $DL_{50}$ of 1800 mg/kg (mice, oral administration). In rats, administered orally at a dose of 100 mg/kg with respect to controls, it causes a diminution of cholesterolemia (from $-20\%$ to $-30\%$), a diminution in the triglycerides ($-15\%$ to $-30\%$) and hepatomegalie ($+10\%$ to $25\%$).

The compounds of Example 1, (4-parachlorophenylsulphonyl-3-γ-dimethylaminopropoxy-1-phenyl-1H-pyrazole), for which the foregoing results show a notable activity, has formed the subject of a more detailed study.

Minimal active dose in normal rats

Utilising the experimental protocol described above, the minimal active doses for hypocholesterolemiant and hypotriglyceridemiant activity have been ascertained. During these tests, under the same conditions, the minimal active doses of clofibrate have also been measured. The results are set in Table VI below.

The product of Example 1 in a dose of 6 mg/kg causes a reduction in cholesterol and triglycerides equal to or greater than that obtained with 50 mg/kg of clofibrate. In these tests, the activity of the product of Example 1 is thus 9 to 10 times greater than that of clofibrate.

Minimal active dose in rats subjected to a hyperlipidic regime

Male Wistar rats weighing 250 g were subjected to a diet increased in lipids comprising 37% butter and 4.5% cholesterol. For each dose of the product studied, a group of 15 animals was utilised. The product was administered daily to each animal for 15 consecutive days. The experiment utilised cross-dosing ranging from 0.625 to 25 mg/kg.

In parallel, under the same conditions, clofibrate was administered in doses of 60 to 300 mg/kg.

A control group was constituted by animals receiving the same diet with the exclusion of all other treatments.

On the 16th day after a fast of 16 hours, the animals were killed and the foregoing determinations were effected.

The results set out in Table VII are expressed in mean percentage variation of the parameters investigated for animals treated with respect to the control group.

The product of Example 1 caused a considerably significant decrease in the three blood factors considered (cholesterol, triglycerides, total lipids) starting at 1.25 mg/kg. At a dosage of 0.625 mg/kg, the cholesterol and total lipids were still significantly reduced.

Under the same conditions, clofibrate is only active in a dose greater than 60 mg/kg. The results obtained at this dose are not statistically significant.

In this experimental model, the compound of Example 1 is thus 50 to 60 times more active than clofibrate.

The hyperlipidic treatment causes hepatomegalie in the animals. It is remarkable that at the minimum active dose (1.25 mg/kg) the product of Example 1 does not increase this hepatomegalie, while clofibrate causes a significant increase in weight of the liver at a dose (60 mg/kg) still insufficient to induce a significant modification in the blood lipidic parameters.

In doses considerably greater than these hypolipemiant doses (20 to 30 mg/kg) administered orally, the compound according to claim 1 is without notable pharmacological action. It is inactive on the central nervous system and the cardiovascular and respiratory systems. It has no ulcerogenic action.

The acute toxicity has been determined by the customary techniques and calculated by the log-probit method.

Orally, the $DL_{50}$ is 670 mg/kg in mice and greater than 1500 mg/kg in rats.

Intraperitoneally, the $DL_{50}$ is 125 mg/kg in mice and 155 mg/kg in rats.

The toxicity on repeated administration has been studied in rats and dogs.

In rats, the product of Example 1 has been administered daily for a month orally, in doses of 2, 5, 5, 10, 30 and 90 mg/kg. For each dose, a group of 10 male animals and 10 female animals was utilised, weighing at the beginning of the experiment from 120 to 170 g. No toxic effect has been observed in the course of the treatment, the increase in weight was normal except at the dose of 90 mg/kg, when there was a slight relaxation in the male animals.

Hematological and biochemical examinations carried out at the end of the experiments have shown comparable results to those observed in the identical groups of untreated animals. Exceptionally, the blood cholesterol and triglycerides had been lowered starting from 10 mg/kg in the male rats.

In dogs, daily oral administration of the compound of Example 1 in doses of 2.5 and 10 mg/kg to beagles during six weeks showed a good tolerance to this example of the product.

No modification in behaviour was observed. The hematological and biochemical constants did not undergo any significant variation. Hypocholesterolemiant action has been found at a dose of 10 mg/kg.

TABLE I

[Structure: R_3, R_4 substituted phenyl—SO_2—pyrazole(with N–phenyl-R_1)—O—CH_2—CH_2—CH_2—N(CH_3)_2, with R_2 on pyrazole]

| | | | | | Bases | | | | | Methanesulphonate |
|---|---|---|---|---|---|---|---|---|---|---|
| | | | | | Formula (P.M.) | | | | | MP °C. |
| Ex No | $R_1$ | $R_2$ | $R_3$ | $R_4$ | MP °C. (Rdt %) | \multicolumn{4}{c|}{Analyses} | (Recrystallisation solvents) |
| | | | | | | C | H | N | S | |

TABLE I-continued

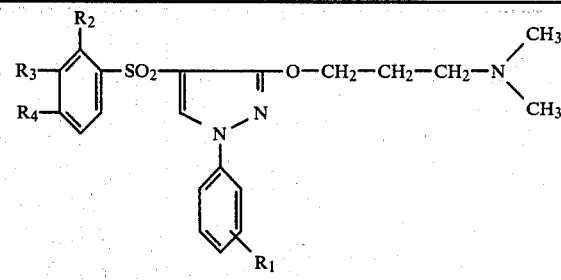

| Ex No | R$_1$ | R$_2$ | R$_3$ | R$_4$ | Bases Formula (P.M.) MP °C. (Rdt %) | | Analyses | | | | Methanesulphonate MP °C. (Recrystallisation solvents) |
|---|---|---|---|---|---|---|---|---|---|---|---|
| 2 | H | H | Cl | H | C$_{20}$H$_{22}$ClN$_3$O$_3$S (419,92) 112° C. (80) (a) | Calc. % F'nd % | C 57,20; 56,91; | H 5,28; 5,40; | N 10,01; 10,06; | S 7,64 8,00 | 164° C. (isopropanol) |
| 3 | H | Cl | H | H | C$_{20}$H$_{22}$ClN$_3$O$_3$S (419,92) 134° C. (80) (b) | Calc. % F'nd % | C 57,20; 56,90; | H 5,28; 5,32; | N 10,01; 10,10; | S 7,64 7,76 | 165° C. acetone (1 v.) ethyl acetate (2 v.) |
| 4 | H | H | H | F | C$_{20}$H$_{22}$FN$_3$O$_3$S (403,27) 75° C. (72) (c) | Calc. % F'nd % | C 59,53; 59,75; | H 5,50; 5,67; | N 10,42; 10,52; | F 4,71 4,79 | 144° C. (ethanol) |
| 5 | H | H | H | Br | C$_{20}$H$_{22}$BrN$_3$O$_3$S (464,38) 114° C. (77) (d) | Calc. % F'nd % | C 51,72; 52,12; | H 4,77; 4,64; | N 9,05; 9,25; | S 6,90 6,70 | 166° C. (ethanol) |
| 6 | H | H | H | —OCH$_3$ | C$_{21}$H$_{25}$N$_3$O$_4$S (415,50) 100° C. (68) (c) | Calc. % F'nd % | C 60,70; 60,95; | H 6,06; 6,26; | N 10,11; 10,17; | S 7,72 7,40 | 163° C. (ethanol) |
| 7 | H | H | H | —CH$_3$ | C$_{21}$H$_{25}$N$_3$O$_3$S (399,50) 111° C. (74) (c) | Calc. % F'nd % | C 63,13; 63,20; | H 6,31; 6,46; | N 10,52; 10,59; | S 8,03 7,96 | 166° C. (ethanol) |
| 8 | H | H | CF$_3$ | H | C$_{21}$H$_{22}$F$_3$N$_3$O$_3$S (453,28) 96° C. (76) (c) | Calc. % F'nd % | C 55,62; 55,63; | H 4,89; 5,03; | N 9,27; 9,23; | S 7,07 7,26 | 140° C. (ethyl acetate) |
| 9 | H | H | H | H | C$_{20}$H$_{23}$N$_3$O$_3$S (385,47) 97° C. (82) (e) | Calc. % F'nd % | C 62,31; 61,91; | H 6,01; 5,93; | N 10,90; 11,15; | S 8,32 8,31 | 165° C. (ethanol) |
| 10 | H | H | Cl | Cl | C$_{20}$H$_{21}$Cl$_2$N$_3$O$_3$S (454,37) 121° C. (69) (c) | Calc. % F'nd % | C 52,86; 52,96; | H 4,66; 4,73; | N 9,25; 9,39; | S 7,06 7,36 | 170° C. (ethanol) |
| 11 | H | Cl | H | Cl | C$_{20}$H$_{21}$Cl$_2$N$_3$O$_3$S (454,37) 130° C. (70) (c) | Calc. % F'nd % | C 52,86; 53,04; | H 4,66; 4,70; | N 9,25; 9,46; | Cl 15,61 15,33 | 152° C. (isopropanol) |
| 12 | H | H | Cl | —OCH$_3$ | C$_{21}$H$_{24}$ClN$_3$O$_4$S (449,95) 96° C. (80) (c) | Calc. % F'nd % | C 56,05; 56,21; | H 5,38; 5,45; | N 9,34; 9,39; | S 7,13 6,99 | 163° C. (ethanol) |
| 13 | (4')Cl | H | H | Cl | C$_{20}$H$_{21}$Cl$_2$N$_3$O$_3$S (454,37) 138° C. (77) (d) | Calc. % F'nd % | C 52,86; 52,96; | H 4,66; 4,70; | N 9,25; 9,28; | S 7,06 7,17 | 126° C. Acetone (3 vol.) Ethyl acetate (7 vol.) |
| 14 | (4')F | H | H | Cl | C$_{20}$H$_{21}$ClFN$_3$O$_3$S (437,91) 136° C. (85) (e) | Calc. % F'nd % | C 54,85; 54,73; | H 4,83; 4,87; | N 9,60; 9,62; | S 4,34 4,80 | 134° C. (acetone) |
| 15 | (4')H$_3$CO | H | H | Cl | C$_{21}$H$_{24}$ClN$_3$O$_4$S (449,95) 103° C. (74) (c) | Calc. % F'nd % | C 56,05; 56,21; | H 5,38; 5,51; | N 9,34; 9,40; | S 7,13 7,26 | 117° C. Acetone (1 vol.) Ethyl acetate (2 vol.) |
| 16 | (4')H$_3$C | H | H | Cl | C$_{21}$H$_{24}$ClN$_3$O$_3$S (433,95) 95° C. (55) (f) | Calc. % F'nd % | C 58,12; 58,06; | H 5,57; 5,60; | N 9,68; 9,53; | S 7,39 7,44 | 172° C. Acetone (1 vol.) (3 vol.) |
| 17 | (3')F$_3$C | H | H | Cl | C$_{21}$H$_{21}$ClF$_3$N$_3$O$_3$S (487,92) | Calc. % F'nd % | C 51,69; 51,71; | H 4,34; 4,37; | N 8,61 8,65 | | 139° C. (Ethyl acetate) |

TABLE I-continued

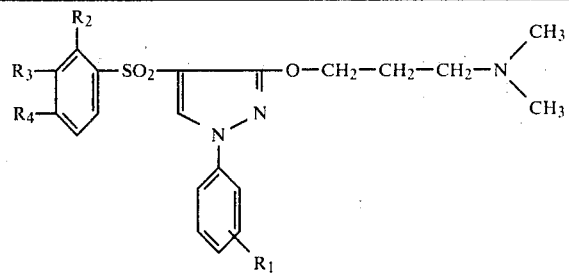

| | | | | | Bases | | Methanesulphonate |
|---|---|---|---|---|---|---|---|
| Ex No | R₁ | R₂ | R₃ | R₄ | Formula (P.M.) MP °C. (Rdt %) | Analyses | MP °C. (Recrystallisation solvents) |
| | | | | | 138° C. (70) (c) | | |

Recrystallisation solvents:
(a) ethanol (1 vol.) - isopropyl oxide (1 vol.);
(b) ethanol (1 vol.) - isopropyl oxide (2 vol.);
(c) isopropyl oxide;
(d) ethanol;
(e) propanol-2;
(f) heptane.

TABLE II

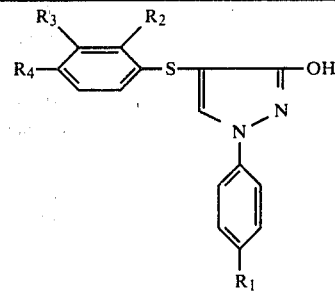

| R₁ | R₂ | R₃ | R₄ | MP °C. | Rdt | Recrystallisation Solvent |
|---|---|---|---|---|---|---|
| H | Cl | H | H | 197 | 31 | ethanol |
| H | H | H | F | 174 | 44 | ethanol |
| H | H | H | H₃C | 179 | 54 | acetone |
| H | H | H | H | 198 | 56 | ethanol |
| H | H | Cl | Cl | 220 | 66 | 2-methoxy-ethanol |
| Cl | H | H | Cl | 212 | 48 | butanone-2 |
| F | H | H | Cl | 196 | 49 | ethanol |
| H₃CO— | H | H | Cl | 234 | 74 | butanone-2 |
| H₃C— | H | H | Cl | 250 | 49 | butanone-2 |

TABLE III

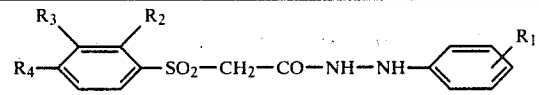

| R₁ | R₂ | R₃ | R₄ | MP °C. | Rdt % | Recrystallisation solvent |
|---|---|---|---|---|---|---|
| (3) F₃C— | H | H | Cl | 168 | 41 | methanol |
| H | H | Cl | H | 169 | 36 | ethanol |
| H | H | H | Br | 175 | 52 | acetone |
| H | H | H | CH₃O— | 168 | 40 | methanol |
| H | H | F₃C— | H | 183 | 54 | ethanol |
| H | H | H | H | 180 | 45 | 2-methoxy-ethanol |
| H | Cl | H | Cl | 162 | 20 | ethanol |
| H | H | Cl | H₃CO— | 190 | 44 | ethanol |

TABLE IV

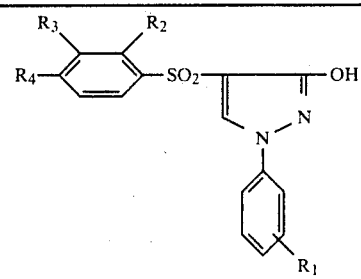

| R₁ | R₂ | R₃ | R₄ | Method (Rdt %) | MP °C. | Formula (P.M.) | Calculated % | | Found % | |
|---|---|---|---|---|---|---|---|---|---|---|
| (3) CF₃— | H | H | Cl | B (77) | 251 | C₁₆H₁₀ClF₃N₂O₃S 402,78 | C H N | 47,71 2,50 6,96 | C H N | 47,84 2,63 7,08 |
| H | H | Cl— | H | B (81) | 224 | C₁₅H₁₁ClN₂O₃S 334,78 | C H N | 53,81 3,31 8,37 | C H N | 54,04 3,34 8,47 |
| H | Cl | H | H | A (88) | 215 | C₁₅H₁₁ClN₂O₃S 334,78 | C H N | 53,81 3,31 8,37 | C H N | 54,10 3,47 8,47 |

TABLE IV-continued

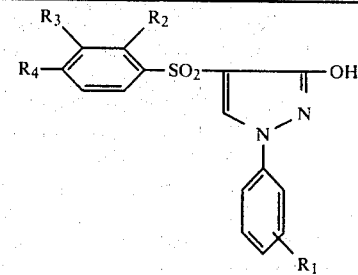

| R₁ | R₂ | R₃ | R₄ | Method (Rdt %) | MP °C. | Formula (P.M.) | Calculated % | Found % |
|---|---|---|---|---|---|---|---|---|
| H | H | H | F | A (92) | 213 | $C_{15}H_{11}FN_2O_3S$ 318,32 | C 56,59<br>H 3,48<br>N 8,80 | C 56,65<br>H 3,64<br>N 8,91 |
| H | H | H | Br | B (84) | 230 | $C_{15}H_{11}BrN_2O_3S$ 379,24 | C 47,50<br>H 2,92<br>N 7,39 | C 47,56<br>H 3,10<br>N 7,44 |
| H | H | H | OCH₃ | B (70) | 288 | $C_{16}H_{14}N_2O_4S$ 330,35 | C 58,17<br>H 4,27<br>N 8,48 | C 57,92<br>H 4,27<br>N 8,49 |
| H | H | H | CH₃ | A (92) | 229 | $C_{16}H_{14}N_2O_3S$ 314,35 | C 61,13<br>H 4,49<br>N 8,91 | C 60,95<br>H 4,45<br>N 8,98 |
| H | H | CF₃ | H | B (78) | 212 | $C_{16}H_{11}F_3N_2O_3S$ 368,33 | C 52,17<br>H 3,01<br>N 7,61 | C 52,50<br>H 3,17<br>N 7,72 |
| H | H | H | H | A (93)<br>B (83) | 248 | $C_{15}H_{12}N_2O_3S$ 300,33 | C 59,98<br>H 4,03<br>N 9,33 | C 60,21<br>H 4,07<br>N 9,25 |
| H | H | Cl | Cl | A (92) | 240 | $C_{15}H_{10}Cl_2N_2O_3S$ 369,23 | C 48,79<br>H 2,73<br>N 7,59 | C 48,67<br>H 2,71<br>N 7,82 |
| H | Cl | H | Cl | B (57) | 211 | $C_{15}H_{10}Cl_2N_2O_3S$ 369,23 | C 48,79<br>H 2,73<br>N 7,59 | C 48,98<br>H 2,86<br>N 7,57 |
| H | H | Cl | OCH₃ | B (91) | 243 | $C_{16}H_{13}ClN_2O_4S$ 364,80 | C 52,67<br>H 3,59<br>N 7,68 | C 52,30<br>H 3,60<br>N 7,77 |
| (4) Cl— | H | H | Cl | A (87) | 260 | $C_{15}H_{10}Cl_2N_2O_3S$ 369,23 | C 48,79<br>H 2,73<br>N 7,59 | C 48,84<br>H 2,76<br>N 7,70 |
| (4) F— | H | H | Cl | A (86) | 261 | $C_{15}H_{10}ClFN_2O_3S$ 352,77 | C 51,07<br>H 2,86<br>N 7,94 | C 51,10<br>H 2,90<br>N 8,02 |
| (4) OCH₃ | H | H | Cl | A (89) | 224 | $C_{16}H_{13}ClN_2O_4S$ 364,80 | C 52,67<br>H 3,59<br>N 7,68 | C 52,99<br>H 3,68<br>N 7,60 |
| (4) CH₃— | H | H | Cl | A (86) | 232 | $C_{16}H_{13}ClN_2O_3S$ 348,80 | C 55,09<br>H 3,76<br>N 8,03 | C 55,09<br>H 3,79<br>N 8,02 |

TABLE V

| Ex. No | DL₅₀ Mice (PO) mg/kg | Dose mg/kg × 4 | Variation % with respect to controls | | |
|---|---|---|---|---|---|
| | | | Cholesterol | Triglycerides | Liver weight |
| 1 | 670 | 10 | −27 | −22 | +25 |
| 2 | 300 < DL₅₀ < 1000 | 10 | −23 | −43 | +20 |
| 3 | 300 < DL₅₀ < 1000 | 10 | −23 | −16 | +9 |
| 4 | 300 < DL₅₀ < 1000 | 10 | −28 | −17 | +27 |
| 5 | DL₅₀ > 1000 | 10 | −20 | −18 | +26 |
| 6 | 300 < DL₅₀ < 1000 | 10 | −10 | 0 | +7 |
| 7 | 300 < DL₅₀ < 1000 | 50 | 0 | −14 | — |
| 8 | 300 < DL₅₀ < 1000 | 10 | −23 | −31 | +20 |
| 9 | 700 | 10 | −18 | −12 | +20 |
| 10 | DL₀ ≧ 1000 | 10 | −25 | −13 | +24 |
| 11 | DL₅₀ = 1000 | 10 | −27 | 0 | +39 |
| 12 | DL₀ ≧ 1000 | 10 | −16 | −13 | +7 |
| 13 | DL₅₀ > 1000 | 10 | −19 | −10 | +21 |
| 14 | 300 < DL₅₀ < 1000 | 10 | −23 | −39 | +26 |
| 15 | DL₅₀ > 1000 | 10 | −5 | −16 | +5 |
| | | 50 | −26 | −17 | +37 |
| 16 | 300 < DL₅₀ < 1000 | 50 | −11 | −7 | — |
| 19 | DL₀ ≧ 1000 | 10 | −33 | −11 | +24 |
| 20 | DL₅₀ > 1000 | 10 | −34 | −18 | +24 |
| 21 | 300 < DL₅₀ < 1000 | 10 | −20 | −16 | +19 |
| 22 | 300 < DL₅₀ < 1000 | 10 | −20 | −24 | +21 |
| 23 | DL₅₀ > 1000 | 10 | −29 | −11 | +30 |

TABLE VI

| Product | Dose P.O. (mg/kg/j) | Variation with respect to controls.% | |
|---|---|---|---|
| | | Cholesterol (seric) | Triglycerides (seric) |
| Ex. No 1 | 2 | −15 | 0 |
| | 6 | −30 | −32 |
| | 12 | −34 | −33 |
| | 25 | −33 | −33 |
| | 50 | −30 | −40 |
| Clofibrate | 12 | 0 | −13 |

TABLE VI-continued

| Product | Dose P.O. (mg/kg/j) | Variation with respect to controls % | |
| --- | --- | --- | --- |
| | | Cholesterol (seric) | Triglycerides (seric) |
| | 25 | −16 | −30 |
| | 50 | −23 | −27 |
| | 100 | −37 | −34 |

TABLE VII

| Product | Dose mg/kg | % variation with respect to controls | | | |
| --- | --- | --- | --- | --- | --- |
| | | Cholesterol | Triglycerides | Total lipids | Hepatomegalie |
| Example No 1 | 0,625 | −23$^x$ | −24 (NS) | −25$^x$ | 0 |
| | 1,25 | −33$^{xx}$ | −39$^{xx}$ | −37$^{xxx}$ | 0 |
| | 2,5 | −48$^{xxx}$ | −46$^{xxx}$ | −54$^{xxx}$ | +9$^{xx}$ |
| | 5 | −57$^{xxx}$ | −48$^{xxx}$ | −61$^{xxx}$ | +25$^{xxx}$ |
| | 10 | −52$^{xxx}$ | −51$^{xxx}$ | −55$^{xxx}$ | +50$^{xxx}$ |
| | 25 | −48$^{xxx}$ | −44$^{xxx}$ | −49$^{xxx}$ | +64$^{xxx}$ |
| Clofibrate | 60 | −20 (NS) | −22 (NS) | −25 (NS) | +18$^{xx}$ |
| | 300 | −36$^{xxx}$ | −59$^{xxx}$ | −41$^{xxx}$ | +49$^{xxx}$ |

$^x$ 0,01 < p < 0,05,
$^{xx}$ 0,001 < p < 0,01
$^{xxx}$ p. ≦ 0,001
(NS) = non-significant

We claim:

1. A compound of the formula:

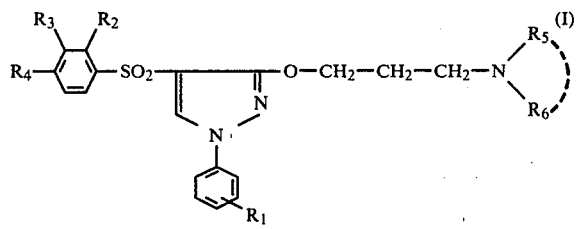

wherein:

$R_1$ represents a hydrogen or halogen atom or a $C_{1-3}$ alkyl, $C_{1-3}$ alkoxy or trifluoromethyl radical in the meta or para position on the phenyl group, $R_2$, $R_3$ and $R_4$ are the same or different and each represents a hydrogen or halogen atom or a $C_{1-3}$ alkyl, $C_{1-3}$ alkoxy or trifluoromethyl group, and $R_5$ and $R_6$ are the same or different and each represents a hydrogen atom or a $C_{1-3}$ alkyl radical or $R_5$ and $R_6$ together represent, with the nitrogen atom to which they are attached, a morpholino, piperidino or pyrrolidino group, and the non-toxic pharmaceutically-acceptable acid addition salts thereof.

2. A compound according to claim 1, wherein $R_1$, $R_2$, $R_3$ and $R_4$ are the same or different and each represents a hydrogen, fluorine, chlorine or bromine atom or a methyl, methoxy or trifluoromethyl group, $R_5$ and $R_6$ are the same or different and each represents a hydrogen atom or a methyl or ethyl group or $R_5$ and $R_6$ together represent, with the nitrogen atom to which they are attached, a morpholino, piperidino or pyrrolidino group.

3. 4-p-Chlorophenylsulphonyl-3-γ-dimethylaminopropoxy-1-phenyl-1H-pyrazole and its non-toxic pharmaceutically-acceptable acid addition salts.

4. A therapeutic composition comprising an antihyperlipemially effective amount of a compound according to claim 1, 2 or 3 in a pharmaceutically acceptable carrier therefor.

5. A therapeutic composition according to claim 4 wherein said compound is present in the amount of from 0.01 g. to 0.05 g.

6. A method of treating hyperlipemia which comprises administering to a host an anti-hyperlipemially effective amount of a compound according to claim 1, 2 or 3.

7. A therapeutic composition comprising an antihypercholesterolemially effective amount of a compound according to claim 1, 2 or 3 in a pharmaceutically acceptable carrier therefor.

8. A therapeutic composition according to claim 7 wherein said compound is present in the amount of from 0.01 g. to 0.05 g.

9. A method of treating hypercholesterolemia which comprises administering to a host an anti-hypercholesterolemially effective amount of a compound according to claim 1, 2 or 3.

* * * * *